(12) United States Patent
Peskin

(10) Patent No.: US 7,815,942 B2
(45) Date of Patent: Oct. 19, 2010

(54) RASAGILINE FORMULATIONS OF IMPROVED CONTENT UNIFORMITY

(75) Inventor: Tirtza Berger Peskin, Raanana (IL)

(73) Assignee: Teva Pharmaceutical Industries, Ltd., Petach Tikva (IL)

(*) Notice: Subject to any disclaimer, the term of this patent is extended or adjusted under 35 U.S.C. 154(b) by 551 days.

(21) Appl. No.: 11/359,324

(22) Filed: Feb. 22, 2006

(65) Prior Publication Data

US 2006/0188581 A1    Aug. 24, 2006

Related U.S. Application Data

(60) Provisional application No. 60/720,908, filed on Sep. 27, 2005, provisional application No. 60/655,622, filed on Feb. 23, 2005.

(51) Int. Cl.
| | |
|---|---|
| A61K 9/14 | (2006.01) |
| A61K 9/20 | (2006.01) |
| A01N 31/36 | (2006.01) |
| A01N 37/30 | (2006.01) |
| A61K 31/135 | (2006.01) |
| C07C 211/00 | (2006.01) |

(52) U.S. Cl. .................. 424/489; 424/464; 514/467; 514/554; 514/657; 564/429

(58) Field of Classification Search ............ None
See application file for complete search history.

(56) References Cited

U.S. PATENT DOCUMENTS

| | | | |
|---|---|---|---|
| 3,513,249 A | 5/1970 | Gittos et al. | |
| 5,387,612 A | 2/1995 | Youdim et al. | |
| 5,444,095 A | 8/1995 | Tatton et al. | |
| 5,453,446 A | 9/1995 | Youdim et al. | |
| 5,457,133 A | 10/1995 | Youdim et al. | |
| 5,486,541 A | 1/1996 | Sterling et al. | |
| 5,519,061 A | 5/1996 | Youdim et al. | |
| 5,532,415 A | 7/1996 | Youdim et al. | |
| 5,576,353 A | 11/1996 | Youdim et al. | |
| 5,599,991 A | 2/1997 | Youdim et al. | |
| 5,668,181 A | 9/1997 | Youdim et al. | |
| 5,744,500 A | 4/1998 | Youdim et al. | |
| 5,767,164 A | 6/1998 | Tatton et al. | |
| 5,786,390 A | 7/1998 | Youdim et al. | |
| 5,844,003 A | 12/1998 | Tatton et al. | |
| 5,891,923 A | 4/1999 | Youdim et al. | |
| 6,126,968 A | 10/2000 | Peskin et al. | |
| 6,277,886 B1 | 8/2001 | Levy et al. | |
| 6,316,504 B1 | 11/2001 | Youdim et al. | |
| 6,462,222 B1 | 10/2002 | Chorev et al. | |
| 6,630,514 B2 | 10/2003 | Youdim et al. | |
| 6,635,667 B2 | 10/2003 | Thomas | |
| 6,682,716 B2* | 1/2004 | Hodges et al. | 424/45 |
| 6,956,060 B2 | 10/2005 | Youdim et al. | |
| 7,396,860 B2 | 7/2008 | Blaugrund et al. | |
| 7,491,847 B2 | 2/2009 | Frenkel | |
| 7,547,806 B2 | 6/2009 | Frenkel et al. | |
| 7,572,834 B1 | 8/2009 | Sterling et al. | |
| 2003/0212145 A1* | 11/2003 | Youdim et al. | 514/657 |
| 2004/0010038 A1 | 1/2004 | Blaugrund et al. | |
| 2004/0052843 A1 | 3/2004 | Lerner et al. | |
| 2004/0127577 A1 | 7/2004 | Blaugrund et al. | |
| 2004/0180088 A1 | 9/2004 | Dudhara et al. | |
| 2005/0026979 A1 | 2/2005 | Ghazzi et al. | |
| 2006/0018957 A1 | 1/2006 | Lerner et al. | |
| 2006/0094783 A1 | 5/2006 | Youdim et al. | |
| 2007/0100001 A1 | 5/2007 | Youdim et al. | |
| 2007/0112217 A1 | 5/2007 | Frenkel et al. | |
| 2007/0232700 A1 | 10/2007 | Blaugrund et al. | |
| 2008/0146676 A1 | 6/2008 | Frenkel et al. | |
| 2008/0161408 A1 | 7/2008 | Frenkel et al. | |
| 2009/0111892 A1 | 4/2009 | Patashnik et al. | |
| 2009/0181086 A1 | 7/2009 | Safadi et al. | |

FOREIGN PATENT DOCUMENTS

| | | |
|---|---|---|
| EP | 0538134 | 4/1993 |
| EP | 0436492 | 6/1994 |
| WO | 9511016 | 4/1995 |
| WO | 9518617 | 7/1995 |
| WO | 9637199 | 11/1996 |
| WO | 9712583 | 4/1997 |
| WO | 9802152 | 1/1998 |
| WO | 2003072055 | 9/2003 |
| WO | 2004045515 | 6/2004 |
| WO | WO 2004/112799 | * 12/2004 |
| WO | 2006057912 | 1/2006 |
| WO | 06091657 | 8/2006 |
| WO | 2007098264 | 8/2007 |
| WO | 2008019871 | 2/2008 |
| WO | 2008131961 | 6/2008 |

OTHER PUBLICATIONS

Burgess et al.(The AAPS Journal 2004; 6(3) Article 20 (http://www.aapsj.org).*
Scientific discussion for the approval of Azilect by FDA, 2005.*
Draft guidance of industry on powder blends and finished dosage units-stratified in-process dosage unit sampling and assessment by FDA, Jan. 21, 2004.*
FDA submission date azilect.*
Finberg and Youdim, (1985) "Modification of Blood Pressure and Nictitating Membrane Response to Sympathetic Amines by Selective Monoamime Oxidase Inhibitors," *Brit. J. Pharmac.* 85(2):541-546.
Finberg et al. (1981) "Selective Irreversible Propargyl Derivative Inhibitors of Monoamine Oxidase (MAO) without the Cheese Effect" *Chem. Abstracts* 94:202499.

(Continued)

*Primary Examiner*—Cherie M Woodward
*Assistant Examiner*—Tigabu Kassa
(74) *Attorney, Agent, or Firm*—John P. White; Cooper & Dunham LLP

(57) ABSTRACT

Disclosed are pharmaceutical preparations of R(+)-N-propargyl-1-aminoindan salts having enhanced content uniformity, processes for preparation of the compositions, and their uses.

37 Claims, 2 Drawing Sheets

OTHER PUBLICATIONS

Finberg et al. (1985) "Modification of Blood Pressure and Nictitating Membrane Response to Sympathetic Amides by Selective Monoamide Oxidase Inhibitors, Types A and B, in the Cat" *Chem. Abstracts* 103:81618.

J. Mendlewicz and M.B.H. Youdim *Brit. J. Psychiat* 1983 142:508-511.

Youdim et al. in Handbook of Experimental pharmacology vol. 90/I (1988) Chapter 3, Trendlenburg and Weiner, eds.

Youdim et al. "Rasagiline (N-propargyl-1R(+)-aminoindan), a Selective and Potent Inhibitor of Mitochondrial Monoamine Oxidase B" *Br. J. Pharmacol.* 2001, 132:500-6.

Youdim et al. *Progress in Medicinal Chemistry* 1984, 21:138-167.

International Preliminary Report of PCT International Application No. PCT/US2006/006252, International Filing Date Feb. 22, 2006.

U.S. Appl. No. 11/791,684, filed May, 24, 2007, Patashnik et al.
U.S. Appl. No. 12/223,794, filed Aug, 7, 2008, Poewe et al.
U.S. Appl. No. 12/283,946, filed Sep. 16, 2008, Lendvai et al.
U.S. Appl. No. 12/231,601, filed Sep. 3, 2008, Oron et al.
U.S. Appl. No. 12/456,642, filed Jun. 19, 2009, Frenkel.
U.S. Appl. No. 12/456,643, filed Jun. 19, 2009, Frenkel at al.
U.S. Appl. No. 12/455,969, filed Jun. 10, 2009, Frenkel et al.
U.S. Appl. No. 12/456,029, filed Jun. 9, 2009, Safadi et al.
U.S. Appl. No. 12/456,031, filed Jun. 9, 2009, Safadi et al.
U.S. Appl. No. 12/455,976, filed Jun. 9, 2009, Safadi et al.
U.S. Appl. No. 12/456,001, filed Jun. 9, 2009, Safadi et al.
U.S. Appl. No. 12/283,022, filed Sep. 8, 2008, Sterling et al.
U.S. Appl. No. 12/283,107, filed Sep. 8, 2008, Sterling et al.
U.S. Appl. No. 12/283,105, filed Sep. 8, 2008, Sterling et al.

Official Action issued in counterpart Chinese Patent Application No. 200680005518.8 on Aug. 21, 2009, with English language translation provided by the Chinese associates.

Official Action issued in counterpart New Zealand Patent Application No. 560660 on Jul. 10, 2009.

U.S. Appl. No. 12/456,166, filed Jun. 12, 2009 (including specification and pending claim set).

Jul. 17, 2006 International Search Report for International Application No. PCT/US06/006252.

International Preliminary Report on Patentability and the Written Opinion of the International Searching Authority for International Application No. PCT/US06/006252.

Sun Ling-ling, "The Comparison of Content Uniformity in Ch.P. With Those in BP \Eurp and USP and JP", Drug Standards of China (2003), vol. 4 (3), p. 13-16.

Feb. 15, 2010 Official Action issued in Russian Patent Application No. 2007135169.

Dec. 31, 2009 Amendment filed in response to the Aug. 21, 2009 Official Action issued in Chinese Patent Application No. 200680005518.8.

Apr. 15, 2010 Communication issued by European Patent Office including a Third Party Observation in connection with European Application No. 06720975.9.

Yalkowsky, S.H., et al. (1990) "Particle Size and Content Uniformity" Pharmaceutical Research. vol. 7 No. 9, pp. 962-966.

European Pharmacopoeia 5.0, Section 2.9.6, "Uniformity of Content of Single-Dose Preparations", p. 234.

Zhang, Y., et al. (1997) "Effect of drug size particle size on content uniformity of low-dose solid dosage. . . ", International Journal of Pharmaceutics. vol. 154, pp. 179-183.

Apr. 14, 2010 Official Action issued in the counterpart Chinese Application No. 200680005518.8, with English language translation provided by the Chinese associates.

* cited by examiner

RASAGILINE FORMULATIONS OF IMPROVED CONTENT UNIFORMITY

This application claims the benefit of U.S. Provisional Application No. 60/720,908, filed Sep. 27, 2005, and U.S. Provisional Application No. 60/655,622, filed Feb. 23, 2005, the entire contents of which are hereby incorporated by reference.

Throughout this application various publications, published patent applications, and published patents are referenced. The disclosures of these publications in their entireties are hereby incorporated by reference into this application in order to more fully describe the state of the art to which this invention pertains.

FIELD OF THE INVENTION

The present invention concerns formulations of the enantiomer R(+)-N-propargyl-1-aminoindan (referred to hereinafter as R(+) PAI or rasagiline) which is a selective irreversible inhibitor of the B-form of the enzyme monoamine oxidase used, for example, for the treatment of Parkinson's disease. The enzyme monoamine oxidase is referred to herein as MAO and the B-form thereof as MAO-B.

BACKGROUND OF THE INVENTION

U.S. Pat. No. 5,532,415 discloses R(+)-N-propargyl-1-aminoindan, its preparation, and various pharmaceutically acceptable salts thereof. U.S. Pat. No. 6,126,968 discloses pharmaceutical compositions comprising R(+)PAI. R(+)PAI and salts thereof have been shown to be selective inhibitors of MAO-B, useful in treating Parkinson's disease and various other conditions.

While not previously identified as a problem for R(+)PAI, a drug substance may be composed of particles which are an impediment, e.g. due to size and shape, to a homogeneous distribution of the drug substance in a tablet blend. If such a drug substance, without further processing, were used in tablet manufacture, the tablets so produced would lack content uniformity and not possess acceptable drug content (e.g., U.S. Pat. No. 5,622,720). Poor content uniformity has been shown to cause a marked decrease in bioavailability. Poor content uniformity can also cause toxicity, if the amount of drug substance is too high.

Due to the increased awareness of bioavailability and safety, compendial authorities such as the United States Pharmacopoeia (USP) have implemented a multi-stage content uniformity test, which includes 1) assaying ten tablets to ensure that the relative standard deviation (RSD) of active content is less than or equal to 6.0% and no value is outside 85-115%; and 2) assaying twenty more tablets to ensure that the RSD for all thirty tablets is less than or equal to 7.8%, no more than one value is outside 85-115% and no value is outside 75-125% of stated content.

SUMMARY OF THE INVENTION

In accordance with the invention it has been surprisingly found that certain particle size distributions have a beneficial effect on the content uniformity of solid pharmaceutical compositions of R(+)PAI. Milling, as well as other methods, can be used to alter the particle size distribution (hereinafter "PSD") of R(+)PAI in order to provide greater uniformity of content of the drug product.

The object of the present invention is to provide content uniformity of drug products comprising R(+)PAI, comprising milling R(+) particles to reduce particle size.

The subject invention provides a mixture of particles of a pharmaceutically acceptable salt of R(+)-N-propargyl-1-aminoindan, wherein more than 90% of the total amount by volume of R(+)-N-propargyl-1-aminoindan salt particles have a size of less than 250 microns.

The subject invention also provides a process for preparing a composition which comprises reducing the particle size of a pharmaceutically acceptable salt of R(+)-N-propargyl-1-aminoindan to a particle size of less than 250 microns.

DETAILED DESCRIPTION OF THE INVENTION

Figure 1:
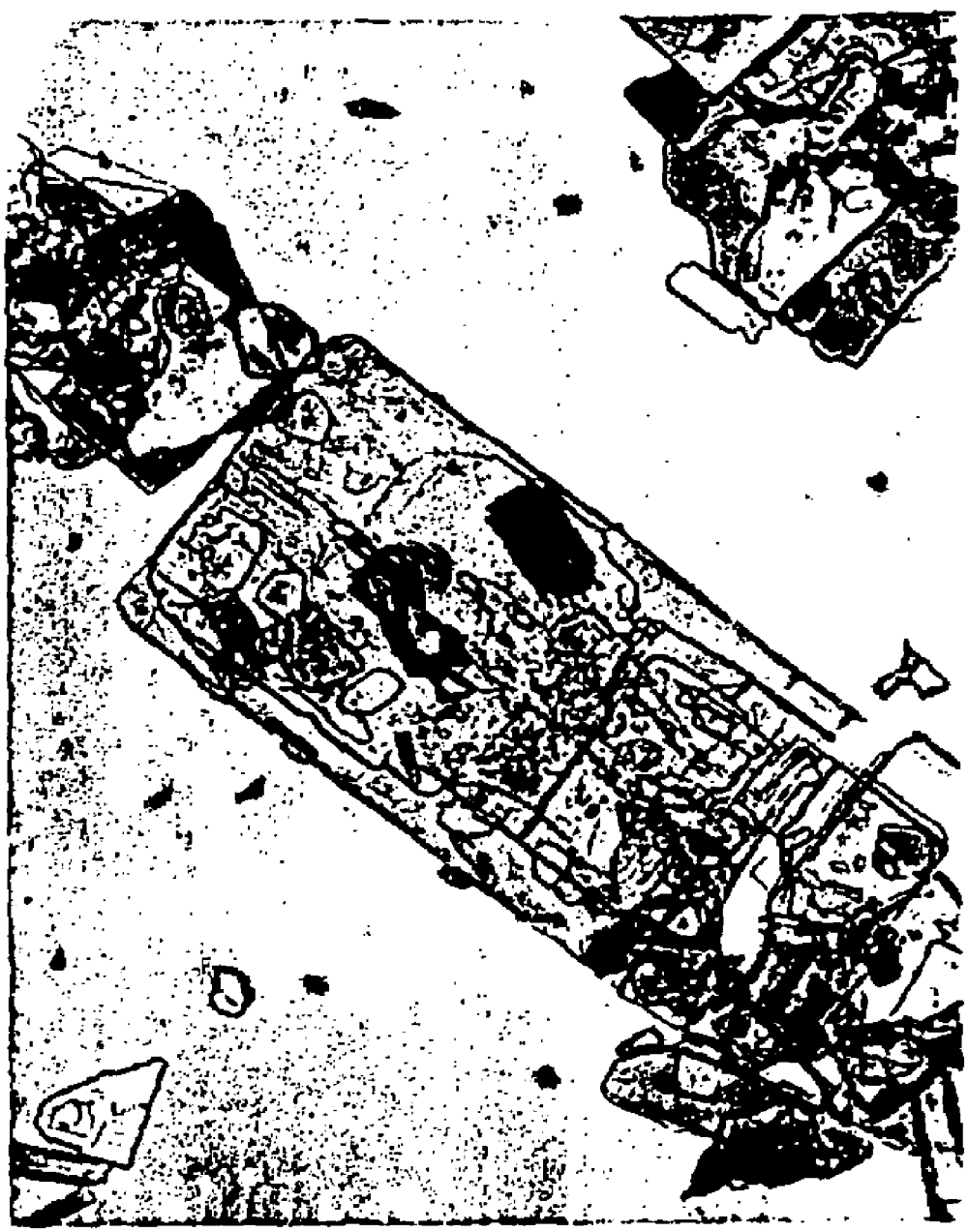
FIG. 1 depicts R(+)PAI mesylate particles before milling. The micrograph was prepared as a paraffin oil suspension and taken at 80× magnification.

The subject invention provides a mixture of particles of a pharmaceutically acceptable salt of R(+)-N-propargyl-1-aminoindan, wherein more than 90% of the total amount by volume of R(+)-N-propargyl-1-aminoindan salt particles have a size of less than 250 microns.

In a further embodiment, more than 90% of the total amount by volume of the R(+)-N-propargyl-1-aminoindan salt particles have a size of less than 240 microns.

In a further embodiment, more than 90% of the total amount by volume of the R(+)-N-propargyl-1-aminoindan salt particles have a size of less than 230 microns.

In a further embodiment, more than 90% of the total amount by volume of the R(+)-N-propargyl-1-aminoindan salt particles have a size of less than 220 microns.

In a further embodiment, more than 90% of the total amount by volume of the R(+)-N-propargyl-1-aminoindan salt particles have a size of less than 210 microns.

In a further embodiment, more than 90% of the total amount by volume of the R(+)-N-propargyl-1-aminoindan salt particles have a size of less than 200 microns.

In a further embodiment, at least 90% of the total amount by volume of the R(+)-N-propargyl-1-aminoindan salt particles have a size of greater than 6 microns.

In a further embodiment, the pharmaceutically acceptable salt is tartrate, esylate, mesylate, or sulfate salt.

In a further embodiment, the pharmaceutically acceptable salt is mesylate salt.

The subject invention also provides a solid composition comprising an amount of R(+)-N-propargyl-1-aminoindan salt particles and a carrier.

In a further embodiment, the solid composition comprises a therapeutically effective amount of the mixture of particles and a pharmaceutically acceptable carrier.

In a further embodiment, the mixture of particles and the carrier constitute a granulate.

In a further embodiment, the composition is in solid dosage form.

In a further embodiment, the composition is in oral dosage form.

In a further embodiment, the oral dosage form is a tablet.

In a further embodiment, the relative standard deviation (RSD) of R(+)-N-propargyl-1-aminoindan salt content among the solid dosage forms is less than 4%.

In a further embodiment, the relative standard deviation (RSD) of R(+)-N-propargyl-1-aminoindan salt content is less than 3%.

In a further embodiment, the relative standard deviation (RSD) of R(+)-N-propargyl-1-aminoindan salt content is less than 2%.

In a further embodiment, the content uniformity is between 95% and 105%.

The subject invention also provides a method of treating a subject afflicted with Parkinson's disease comprising administering to the subject any of the above compositions.

The subject invention also provides a process for preparing a composition which comprises reducing the particle size of a pharmaceutically acceptable salt of R(+)-N-propargyl-1-aminoindan to a particle size of less than 250 microns.

In a further embodiment, the particle size is less than 200 microns.

In a further embodiment, the reducing step comprises comminution of the particles of the pharmaceutically acceptable salt of R(+)-N-propargyl-1-aminoindan.

In a further embodiment, the process further comprises admixing the particles of R(+)-N-propargyl-1-aminoindan with a carrier to form a granulate.

In a further embodiment, the blend uniformity of the granulate is between 90% and 110% and the relative standard deviation (RSD) of the blend uniformity is less than 2%.

In a further embodiment, the blend uniformity is between 95% and 105% and the relative standard deviation of the blend uniformity is less than 2%.

In a further embodiment, the process further comprises compressing the granulate comprising particles of a pharmaceutically acceptable salt of R(+)-N-propargyl-1-aminoindan having a particle size of less than 250 microns into a solid dosage form.

In a further embodiment, the solid dosage form is a tablet.

In a further embodiment, the process for preparing a solid composition comprises:
a) subjecting a batch of particles of a pharmaceutically acceptable salt of R(+)-N-propargyl-1-aminoindan to comminution;
b) admixing the product of step a) with a carrier to form a granulate;
c) determining the blend uniformity of the granulate; and
d) forming the granulate into the composition from the granulate only if the blend uniformity of the granulate satisfies a predetermined criteria, so as to prepare the composition.

In a further embodiment, the predetermined criteria are a blend uniformity of between 90% and 110% and a relative standard deviation of less than 2%.

In a further embodiment, the predetermined criteria are a blend uniformity of between 95% and 105% and a relative standard deviation of less than 2%.

In a further embodiment, the forming step c) comprises preparation of a solid dosage form.

In a further embodiment, the forming step c) comprises preparation of an oral dosage form.

In a further embodiment, the oral dosage form is a tablet.

In a further embodiment, the process further comprises determining the content uniformity of the solid dosage form.

In a further embodiment, the process further comprises a step of qualifying the solid dosage form as an acceptable composition only if the content uniformity satisfies a predetermined criterion.

In a further embodiment, the predetermined criterion is a content uniformity of between 95% and 105%.

In a further embodiment, the predetermined criterion is a relative standard deviation of content uniformity of less than 4%.

In a further embodiment, the predetermined criterion is a relative standard deviation of content uniformity of less than 3%.

In a further embodiment, the predetermined criterion is a relative standard deviation of content uniformity of less than 2%.

In a further embodiment, the process further after step c) comprises a step of reducing the size of particles of the pharmaceutically acceptable salt of R(+)-N-propargyl-1-aminoindan of any batch which does not satisfy the predetermined criteria.

In a further embodiment, step b) comprises reducing the size of particles of the pharmaceutically acceptable salt of R(+)-N-propargyl-1-aminoindan.

In a further embodiment, the reducing step comprises milling the particles of the pharmaceutically acceptable salt of R(+)-N-propargyl-1-aminoindan.

The subject invention also provides a solid pharmaceutical composition comprising a therapeutically effective amount of a pharmaceutically acceptable salt of R(+)-N-propargyl-1-aminoindan prepared by any of the processes above.

The subject invention also provides a method of treating a subject afflicted with Parkinson's disease comprising administering to the subject the pharmaceutical composition of the subject invention in an amount effective to treat Parkinson's disease in the subject.

The subject pharmaceutical compositions may be used alone to treat Parkinson's disease, or alternatively, they may be used as an adjunct to the conventional L-DOPA treatments.

Methods of treatment of Parkinson's disease which combine the use of the subject pharmaceutical compositions with other drugs, such as dopamine agonists, bromocryptine, pergolide, lisuride, as well as catecholamine oxidase methyl transferase inhibitors are also within the scope of the subject invention.

Such compositions may comprise the compound of R(+) PAI or pharmaceutically acceptable acid addition salts thereof, together with pharmaceutically acceptable carriers and/or excipients. In the practice of this invention, pharmaceutically acceptable salts include, but are not limited to, the mesylate, maleate, fumarate, tartrate, hydrobromide, esylate, p-tolunesulfonate, benzoate, acetate, phosphate and sulfate salts. Particles of R(+)PAI salts are referred to herein as "R(+)PAI particle" or active ingredient or the drug substance.

The compositions may be prepared as medicaments to be administered orally, parenterally, rectally or transdermally. Suitable forms for oral administration include tablets, compressed or coated pills, dragees, sachets, hard or soft gelatin capsules, sublingual tablets, syrups and suspensions; for parenteral administration the invention provides ampoules or vials that include an aqueous or non-aqueous solution or emulsion; for rectal administration there are provided suppositories with hydrophilic or hydrophobic vehicles; and for topical application as ointments and transdermal delivery there are provided suitable delivery systems as known in the art.

Specific examples of pharmaceutical acceptable carriers and excipients that may be used to formulate oral dosage forms of the present invention are described, e.g., in U.S. Pat. No. 6,126,968 to Peskin et al., issued Oct. 3, 2000. Techniques and compositions for making dosage forms useful in the present invention are described-in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.).

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, dicalcium phosphate, calcium sulfate, mannitol, sorbitol, microcrystalline cellulose and the like. Suitable binders include starch, gelatin, natural sugars such as glucose or beta-lactose, corn starch, natural and synthetic gums such as acacia, tragacanth, or sodium alginate, povidone, carboxymethylcellulose, polyethylene glycol, waxes, and the like. Lubricants used in these dosage forms include sodium oleate, sodium stearate, sodium benzoate, sodium acetate, sodium chloride, stearic acid, sodium stearyl fumarate, talc and the like. Disintegrators include, without limitation, starch, methyl cellulose, agar, bentonite, xanthan gum, croscarmellose sodium, sodium starch glycolate and the like.

R(+)PAI is intended to be formulated as an oral solid dosage form, specifically tablet form. Tablet formation most commonly involves compression of a measured volume of the drug product, in granulated powder form, by two punches within a die cavity. The tablet assumes the size and shape of the punches and die cavity. (Rudnic et al. Chpt. 45, *Remington's Pharmaceutical Sciences*, 20$^{th}$ Edition, Lippincott Williams & Wilkins, Baltimore, Md. (2000))

A major concern that arose during the formulation process for R(+)PAI was the difficulty of maintaining uniformity of content of the drug product. The unit dose amount of R(+)PAI is quite low relative to the total weight of the tablet; a typical formulation, for example, comprised of 1 mg of R(+)PAI in a tablet with total weight of over 200 mg. As such, a small fluctuation in the amount of R(+)PAI due to flowability or segregation problems could result in a large percent deviation from 1 mg.

Another cause for such concern is the large and irregular shape of R(+)PAI particles that results from salt crystallization. Although drug substance is normally measured by weight, volume also plays an important role during the tablet formation process. As such, large and irregularly-shaped particles can easily decrease content uniformity. Particle size, therefore, was decreased and made more uniform in order to ensure uniformity of tablet content.

Reduction of particle size is achieved via comminution, or a mechanical process of reducing the size of particles which includes any one or more of cutting, chipping, crushing, grinding, milling, micronizing, and trituration. Ordinarily, the most common motivation for decreasing particle size via comminution is to increase dissolution. The rate of dissolution of small particles is usually faster than that of large particles because a greater surface area of the drug substance is in contact with the liquid medium. This effect has been highlighted by the superior dissolution rate observed after micronization of sparingly soluble drugs. (Abdou et al. Chpt. 35, *Remington's*, infra.) Therefore, when formulating a drug with a low dissolution rate, it is desirable to decrease particle size in order to increase dissolution and thus facilitate rapid gastrointestinal or oral absorption.

R(+)PAI mesylate, however, is readily soluble in water (approximately 617 mg/mL at 25° C.). Such fast dissolution behavior minimizes concerns related to gastrointestinal absorption and bioavailability. Hence, increasing solubility is not a motivating factor for comminution of R(+)PAI.

In such cases where drug substances already possess high solubility, particle size reduction may be inadvisable and even deleterious. Increasing surface area by comminution can increase degradation rates of the active. As discussed in U.S. Pat. No. 6,126,968, R(+)PAI is susceptible to degradation. Drug substances may also undergo unwanted polymorphic transformation during comminution. As a result, comminution may affect the efficacy and safety of a drug substance.

The disadvantage of comminution is illustrated by the drug Nitrofurantoin, an antibacterial drug used in the treatment of uncomplicated lower urinary-tract infections. Its absorption rate is dependent on crystal size. The macrocrystalline form of Nitrofurantoin has slower dissolution and absorption rates, produces lower serum concentrations and takes longer to achieve peak concentration in urine than the microcrystalline form (Martindale). However, an 18-year study has shown that the microcrystalline form produces negative side effects ("adverse events") such as nausea and gastro-intestinal problems. Such negative side effects did not manifest in subjects who took a macrocrystalline form dosage. (Brumfitt, W. and J. M. T. Hamilton-Miller, *J. Antimicrobial Chemotherapy* 42:363-371 (1998))

In spite of the fact that comminution is unnecessary to increase the solubility of readily-soluble R(+)PAI, it was unexpectedly found that reduction of particle size, via comminution, improved content uniformity of the tablet.

A method for comminution is determined based on the characteristics of the material, such as initial particle size and desired particle size, as well as melting point, brittleness, hardness, and moisture content (O'Conner et al. Chpt. 37, *Remington's*, infra.). Milling has been determined to be suitable to alter the PSD of R(+)PAI in order to provide uniformity of content of the drug product.

Many analytical tools are available to determine PSD. In the early development stage, the analysis of PSD was performed through microscopic and sieve analysis. Laser diffraction was chosen as the final analytical method for measuring the PSD. Because the large particles were of major concern, the important characteristics of the PSD were the d(0.9), which is the size, in microns, below which 90% of the particles by volume are found, and the d(0.1), which is the size, in microns, below which 10% of the particles by volume are found.

"Blend uniformity," as used herein, refers to the homogeneity of granulate including R(+)PAI particles before tablet formulation, and can represent either one sample or the average of more than one sample.

"Content uniformity," as used herein, refers to the homogeneity of the R(+)PAI content among dosage forms, e.g. tablets, after formulation.

Figure 2:
FIG. 2 depicts R(+)PAI mesylate particles after milling. The micrograph was prepared as a paraffin oil suspension and taken at 80× magnification.

"Particle," as used herein, refers to an aggregated physical unit of the R(+)PAI compound, i.e., a piece or grain of the R(+) PAI. For example, FIGS. 1 and 2 provide photographic representations of various R(+) PAI particles.

"Relative standard deviation" or "RSD," as used herein, refers to a measurement of how precise each measurement of blend uniformity or content uniformity is, i.e., how much each individual unit deviates from the group.

Experimental Details

EXAMPLE 1

R(+)PAI mesylate samples before milling contain large, irregular, plate-shaped particles of various sizes (See FIG. 1). PSDs of four different batches were measured before milling and after milling. The PSDs were measured using Malvern Laser Diffraction, using the Mastersizer S model. Laser diffraction relies on the fact that diffraction angle of light is inversely proportional to particle size. Properties of particles are measured and interpreted as measurements of a sphere (a sphere being the only shape that can be described by one unique number). In addition, laser diffraction calculates a particle size distribution based around volume terms, thus eliminating particle count from the determination of particle size. The Masterizer S model measures particles using a single technique and a single range setting.

The values in the table represent averages of two measurements. Each measurement was taken after 3 minutes of recirculation with the speed control at the 14 hour position. The dilution medium was a 1% solution of dioctyl sulfosuccinate sodium salt in n-hexane. The concentration of drug substance used in the measurements was between 0.05% and 0.35% by volume. The results were confirmed with microscopic observation. For optical microscopy, an emulsion or suspension, diluted or undiluted, was mounted on a slide or ruled cell. The microscope eyepiece was fitted with a micrometer by which the size of the particles may be estimated. The results of the experiment are shown in Table 1.

D(0.1) is the particle size, in microns, below which 10% by volume distribution of the population is found, and d(0.9) is the particle size, in microns, below which 90% by volume distribution of the population is found.

TABLE 1

| Batch number before milling/after milling | D197/197 | D297/297 | D222/223 | D211/212 |
|---|---|---|---|---|
| d (0.1) before milling | 21 | 20 | 18 | 104 |
| d (0.9) before milling | 443 | 386 | 573 | 598 |
| d (0.1) after milling | 14 | 11 | 10 | 16 |
| d (0.9) after milling | 168 | 160 | 156 | 189 |

Results:

From Example 1 it is evident that milling of the drug substance alters the PSD and smaller particles are thereby obtained.

EXAMPLE 2

Formulations were prepared according to the following process, using several batches of R(+)PAI with controlled PSD determined by the method used in Example 1:

| | |
|---|---|
| Rasagiline Mesylate | 1.56 mg |
| Pregelatinized Starch | 20.0 mg |
| Talc | 4.0 mg |

-continued

| | |
|---|---|
| Mannitol | 159.24 mg |
| Starch | 20.0 mg |
| Colloidal Anhydrous Silica | 1.2 mg |
| Stearic Acid | 4.0 mg |

All excipients except for the lubricants were mixed with R(+)PAI mesylate, and water was added during mixing. When the granulate was homogenous, it was dried in a fluid bed drier. The dried granulate was then milled in an oscillating granulator. A lubricated blend was then prepared using a tumbler blender. The mixture was then pressed into tablets weighing 210.0 g.

Average blend uniformity and content uniformity of the tablets were determined. Average blend uniformity of each batch of the granulate was determined by taking 10 samples that represent the upper, middle and lower layer of each batch of the final blend (before tableting,) performing an HPLC assay to measure the amount of active ingredient in the samples, and comparing the amount of active ingredient in each sample to the labeled amount of active ingredient. The standard deviation and relative standard deviation were then determined according to the following formulae:

$$s = \left[ \frac{\sum (x_i - \overline{X})^2}{n-1} \right]^{1/2}$$

$$RSD = \frac{100s}{\overline{X}}$$

In the above formulae, s is the standard deviation; RSD is the relative standard deviation; $x_1, x_2, x_3 \ldots x_n$ are individual amounts of the tested samples expressed as percentages of the labeled amount of drug substance in each sample; X(bar) is the mean of the values obtained from the samples tested, expressed as a percentage of the labeled amount of drug substance in each sample; and n is the number of units tested.

Content uniformity of the tablets was determined using 10 random tablets, by performing an HPLC assay to measure the amount of active ingredient in each tablet, and comparing the amount of active ingredient in each tablet to the labeled amount of active ingredient. The standard deviation and relative standard deviation were determined as above.

d(0.1) and d(0.9) were determined as in example 1. The results are shown in Table 2.

TABLE 2

| Drug Substance Batch Number | 100 | 200 | 300 | 300 |
|---|---|---|---|---|
| Drug Product Batch Number | 021 | 022 | 023 | 063 |
| d (0.1) (microns) | 12.5 | 12.9 | 12.1 | 12.1 |
| d (0.9) (microns) | 190.3 | 111.9 | 121.0 | 121.0 |
| Blend uniformity/ RSD (percent) | 98.2/1.7 | 99.8/0.8 | 98.7/1.1 | 98.1/0.7 |
| Content uniformity/ RSD (percent) | 99.3/1.6 | 99.0/1.4 | 98.6/1.3 | 100.6/1.2 |

Results:

Content uniformity of the batches tested ranged from 98.6% to 100.6%. RSD (relative standard deviation, expressed as a percentage of the mean) was lower than 2.0% for all of the batches of tablets, indicating that the uniformity of tablets was high despite the small amount of active ingredient in each tablet. As such, these results would pass the acceptance criteria set by the first stage of the USP content uniformity test.

What is claimed is:

1. A mixture of particles of a pharmaceutically acceptable salt of R(+)-N-propargyl-1-aminoindan, wherein more than 90% of the total amount by volume of R(+)-N-propargyl-1-aminoindan salt particles have a size of greater than 6 microns and less than 250 microns.

2. The mixture of claim 1, wherein more than 90% of the total amount by volume of the R(+)-N-propargyl-1-aminoindan salt particles have a size of greater than 6 microns and less than 220 microns.

3. The mixture of claim 2, wherein more than 90% of the total amount by volume of the R(+)-N-propargyl-1-aminoindan salt particles have a size of greater than 6 microns and less than 200 microns.

4. The mixture of claim 1, wherein the pharmaceutically acceptable salt is tartrate, esylate, mesylate, or sulfate salt.

5. The mixture of claim 4 wherein the pharmaceutically acceptable salt is mesylate salt.

6. A solid composition comprising an amount of the mixture of particles of claim 1 and a carrier.

7. The solid composition of claim 6, comprising a therapeutically effective amount of the mixture of particles and a pharmaceutically acceptable carrier.

8. The solid composition of claim 6, wherein the mixture of particles and the carrier constitute a granulate.

9. The composition of claim 8, in a solid dosage form.

10. The composition of claim 9, in oral dosage form.

11. The composition of claim 10, wherein the oral dosage form is a tablet.

12. The composition of claim 9, wherein the relative standard deviation (RSD) of R(+)-N-propargyl-1-aminoindan salt content among the solid dosage forms is less than 4%.

13. The composition of claim 12, wherein the relative standard deviation (RSD) of R(+)-N-propargyl-1-aminoindan salt content is less than 3%.

14. The composition of claim 13, wherein the relative standard deviation (RSD) of R(+)-N-propargyl-1aminoindan salt content is less than 2%.

15. The composition of claim 9, wherein the content uniformity is between 95% and 105%.

16. A method of treating a subject afflicted with Parkinson's disease comprising administering to the subject a solid composition comprising a carrier, and a therapeutically effective amount of a mixture of particles of a pharmaceutically acceptable salt of R(+)-N-propargyl-1-aminoindan, wherein more than 90% of the total amount by volume of R(+)-N-propargyl-1-aminoindan salt particles have a size of greater than 6 microns and less than 250 microns.

17. A process for preparing a composition which comprises reducing the particle size of a pharmaceutically acceptable salt of R(+)-N-propargyl-1-aminoindan to a particle size of greater than 6 microns and less than 250 microns.

18. The process of claim 17, wherein the particle size is less than 200 microns.

19. The process of claim 17, wherein the reducing step comprises comminution of the particles of the pharmaceutically acceptable salt of R(+)-N-propargyl-1-aminoindan.

20. The process of claim 17, further comprising admixing the particles of R(+)-N-propargyl-1-aminoindan with a carrier to form a granulate.

21. The process of claim 20, wherein the blend uniformity of the granulate is between 90% and 110% and the relative standard deviation (RSD) of the blend uniformity is less than 2%.

22. The process of claim 21, wherein the blend uniformity is between 95% and 105% and the relative standard deviation of the blend uniformity is less than 2%.

23. The process of any claim 20, further comprising compressing the granulate comprising the particles of a pharmaceutically acceptable salt of R(+)-N-propargyl-1-aminoindan having a particle size of less than 250 microns into a solid dosage form.

24. The process of claim 23, wherein the solid dosage form is a tablet.

25. A process for preparing a solid composition comprising:
    a) subjecting a batch of particles of a pharmaceutically acceptable salt of R(+)-N-propargyl-1-aminoindan to comminution;
    b) admixing the product of step a) with a carrier to form a granulate;
    c) determining the blend uniformity of the granulate; and
    d) forming the composition from the granulate only if the blend uniformity of the granulate satisfies a predetermined criteria, so as to prepare the composition.

26. The composition of claim 6, wherein the pharmaceutically acceptable salt is tartrate, esylate, mesylate, or sulfate salt.

27. The composition of claim 26, wherein the pharmaceutically acceptable salt is mesylate salt.

28. The composition of claim 11, wherein the pharmaceutically acceptable salt is tartrate, esylate, mesylate, or sulfate salt.

29. The composition of claim 28, wherein the pharmaceutically acceptable salt is mesylate salt.

30. The composition of claim 12, wherein the pharmaceutically acceptable salt is tartrate, esylate, mesylate, or sulfate salt.

31. The composition of claim 30, wherein the pharmaceutically acceptable salt is mesylate salt.

32. The composition of claim 15, wherein the pharmaceutically acceptable salt is tartrate, esylate, mesylate, or sulfate salt.

33. The composition of claim 32, wherein the pharmaceutically acceptable salt is mesylate salt.

34. The method of claim 16, wherein the pharmaceutically acceptable salt is tartrate, esylate, mesylate, or sulfate salt.

35. The method of claim 34, wherein the pharmaceutically acceptable salt is mesylate salt.

36. The process of claim 24, wherein the pharmaceutically acceptable salt is tartrate, esylate, mesylate, or sulfate salt.

37. The process of claim 36, wherein the pharmaceutically acceptable salt is mesylate salt.

* * * * *